United States Patent
Schoeffel

(10) Patent No.: US 6,997,714 B1
(45) Date of Patent: Feb. 14, 2006

(54) METHOD AND APPARATUS FOR EVACUATION OF ROOT CANAL

(76) Inventor: G. John Schoeffel, P.O. Box 3810, Dana Point, CA (US) 92629

( * ) Notice: Subject to any disclaimer, the term of this patent is extended or adjusted under 35 U.S.C. 154(b) by 169 days.

(21) Appl. No.: 10/387,804

(22) Filed: Mar. 13, 2003

(51) Int. Cl.
*A61C 5/02* (2006.01)
(52) U.S. Cl. .................. 433/224; 433/81; 128/221
(58) Field of Classification Search ........... 433/224, 433/81, 91; 604/187
See application file for complete search history.

(56) References Cited

U.S. PATENT DOCUMENTS

| 4,276,880 | A | | 7/1981 | Malmin | |
|---|---|---|---|---|---|
| 6,235,008 | B1 | * | 5/2001 | Heinzelman et al. | ....... 604/279 |
| 2002/0142260 | A1 | * | 10/2002 | Pond | ............................ 433/81 |
| 2004/0043356 | A1 | * | 3/2004 | Schlussel | ..................... 433/91 |

OTHER PUBLICATIONS

Ingle, John I. and Bakland, Leif I., "Endodontics", Jun. 2002, pp. 502-503.

* cited by examiner

*Primary Examiner*—Cary E. O'Connor
*Assistant Examiner*—Candice C. Stokes
(74) *Attorney, Agent, or Firm*—Blakely Sokoloff Taylor & Zafman

(57) ABSTRACT

After the working of a root canal by instruments to remove material and shape the walls of the canal, a microaspirator is inserted into the canal extending to about 5 mm from the apex and a vacuum is applied which sucks up some of the debris in the canal. Then a tube is inserted in the exposed opening of the canal with the vacuum still applied. Irrigant is supplied by the needle by an opening in the needle, but not under pressure. As the irrigant is supplied, it is drawn down to end of the aspirator by the vacuum which exists in the canal and up into the aspirator. The aspirator is removed and a second, smaller aspirator with a hole in its wall near its sealed end is inserted into the canal until it almost reaches the apex.

5 Claims, 4 Drawing Sheets

METHOD AND APPARATUS FOR EVACUATION OF ROOT CANAL

1. Field of the Invention

The invention is in the field of endodontics, more particularly methods and apparatus used during root canal procedures.

2. Background of the Invention

To preserve a tooth that has or could develop a diseased pulp cavity, it is necessary to prevent bacterial proliferation within the root or pulp canal of the tooth by enlarging the canal without excessively weakening the root's wall by using endodontic files, bores, reamers or other instrumentation in order to: 1) mechanically remove as much of the root canal contents as is possible and 2) allow the introduction of irrigants into the root canal space that dissolve and disinfect organic debris, thus minimizing the presence of bacteria, as well as clearing the walls of the root canal of calcific debris created during instrumentation. After completing steps 1 and 2, the root canal is typically filled or obturated with a material such as gutta-percha and a sealer to occlude the pulp cavity and thus seal the root canal. This procedure is referred to as root canal therapy.

Irrigation assists in removing debris and necrotic material remaining after the endodontic files bores, and reamers used during the removing and shaping steps of the procedure. Although, the irrigant preferably is capable of dissolving or disrupting soft tissue remnants to permit their removal, the irrigant may be any suitable liquid such as water or various alcohols. More particularly, although some degree of debridement is preferred, any fluid may be used to flush debris from the root canal. General examples of appropriate irrigants include hydrogen peroxide and sodium hypochlorite.

In order to ensure that as much of the debris and necrotic material as possible is removed, the irrigant is typically applied under pressure using a syringe and a needle inserted into the canal as shown in FIG. 2a. FIG. 2b shows an enlarged view of the end of the needle shown in FIG. 2a. However, as reported in *Endodontics, 5th Edition*, by John I. Ingle and Leif K. Bakland published June 2002, pages 502–503, it is important that the needle fit loosely in the canal to allow backflow. It is also reported that there is little flushing beyond the depth of the needle unless the needle is bound in the canal and the irrigant forcibly ejected which is undesirable due to the danger of an irrigant such as sodium hypochlorite breaching the apex of the canal and entering the periapical tissue. However, unless the end of the needle is near the apex, the portion of the canal from the apex to the end of the needle cannot be effectively irrigated. But placing the end of the needle near the apex increases the likelihood of the irrigant, which is applied under pressure, entering the periapical tissue. This can be a source of post treatment endodontic pain for the patient. Futhermore, if a significant quantity of an irrigant like sodium hypochlorite is accidently injected into the periapical tissue, morbid clinical complication can occur including excruciating pain, immediate swelling (ballooning) of the tissue and profuse bleeding.

Existing techniques attempt to address this problem by using very small needles to get close to the apex while still fitting loosely in the canal to allow backflow or using an instrument to move some of the irrigant towards the apex with the irrigant no longer under pressure. However, neither technique completely solves the problem. Even the tip of the smallest needles that deliver irrigants under pressure must be kept a safe distance (approximately 4–6 mm) away from the apex in order to avoid accidentally forcing irrigants into the periapical tissue. This safety issue most often results in an area or zone between the apex and needle tip devoid of irrigant. Use of an instrument to force the irrigant through this zone towards the apex is very time consuming and also does not guarantee that the irrigant has flushed the canal all the way to the apex without going too far.

SUMMARY OF THE INVENTION

The present invention addresses the prior art problems of inadequate delivery of the irrigant to the apex of the canal resulting in an incomplete cleaning of the canal and penetration of the irrigant past the apex into the periapical tissue resulting in treatment complications. According to the invention, after the working of the canal by instruments to remove material and shape the walls of the canal, a microaspirator is inserted into the canal extending to about 5 mm from the apex and a vacuum is applied which begins to suck up the debris inside the canal. As this vacuum is applied, a small tube used to deliver irrigant is placed just inside the coronal opening of the root canal. Irrigant is passively flowed into the opening of the root canal, but not under pressure. As the irrigant is supplied, it is drawn to the source of the vacuum causing it to cascade down the walls of the root canals, into the tip of the aspirator and out through the vacuum system. After several minutes of irrigant cascading down the canal walls, the aspirator is removed and a second, smaller aspirator with a hole in its wall near the tip is inserted into the canal until it virtually touches the apical tissue, but unlike the prior art, extending it past the apex does not cause irrigant to enter the periapical tissue because as soon as the hole enters the periapical tissue, since it is no longer in an open space, the vacuum created by the aspirator is not present.

BRIEF DESCRIPTION OF THE DRAWINGS

FIG. 3b is an expanded view taken along line 3b–3b of FIG. 3a.

FIG. 4b is an expanded view taken along line 4b–4b of FIG. 4a.

DETAILED DESCRIPTION OF THE INVENTION

Figure 1:
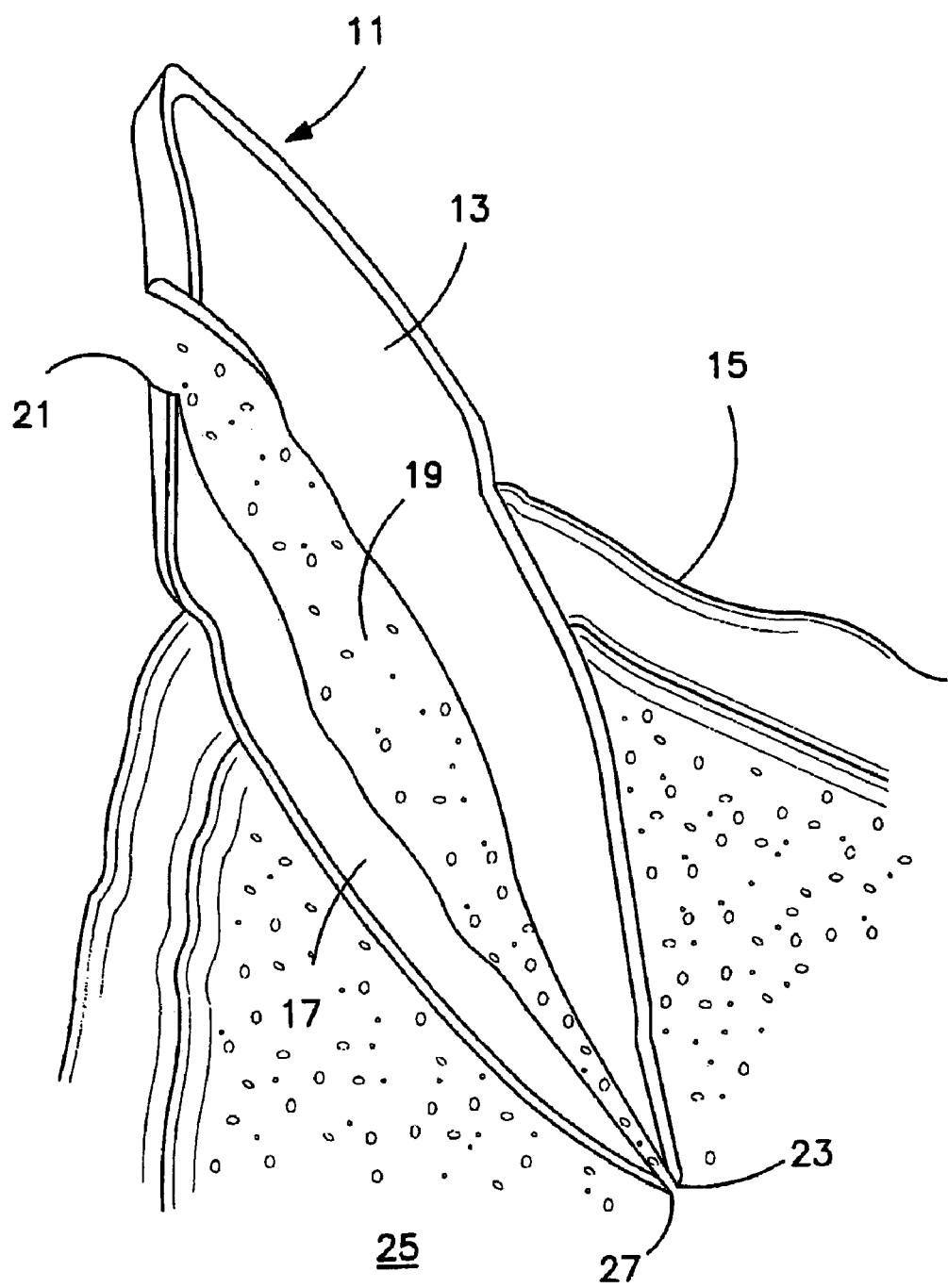
FIG. 1 is a cut away side view of a tooth showing its root canal and periapical tissue.
Figure 2:
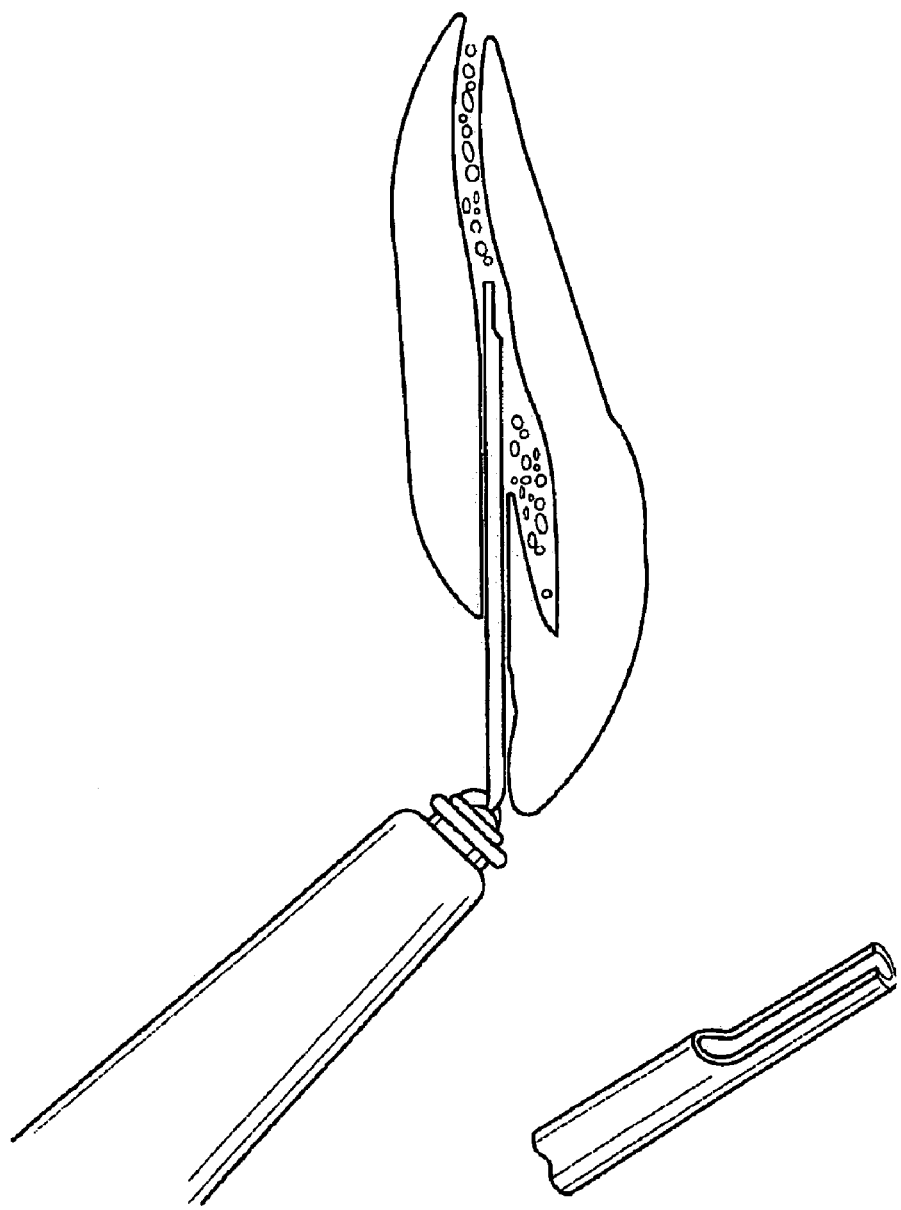
FIGS. 2a and 2b show a prior art endodontic irrigation system.

FIG. 1 illustrates a cutaway portion of a human tooth 11 as it may appear after a portion of a root canal procedure has been completed, namely wherein as much of the pulp material as is possible has been removed by instrumentation. The tooth 11 includes a crown portion 13 which is generally the exterior portion extending past gums 15. The interior portion of the tooth extending past the other side of gums 15 is referred to as the root 17. In approximately the middle of the root extending almost the entire length of the root is the root canal 19 which extends from one end 21 near the crown portion of the tooth to an apex 23 at the tip of root 17. As shown in FIG. 1, the non-visible portion of tooth 11 extending past gums 15 is surrounded by periapical tissue 25.

Of course, prior to the initiation of the root canal procedure, the apical foramen 27 located at or very near the root apex 23 is the only opening into the root canal.

After the instrumentation phase of the root canal procedure has been completed, there is a large quantity, both in terms of size and amount, of debris within the root canal.

According to the present invention, after the instrumentation step, cleansing of the root canal is performed in two phases. The first phase is referred to as gross evacuation of the coronal portion of the root canal which is the portion of the root canal 19 beginning approximately 4–5 mm from apex 23. The second phase is referred to as apical evacuation for cleaning the final 4–5 mm of the root canal.

Figure 3B:
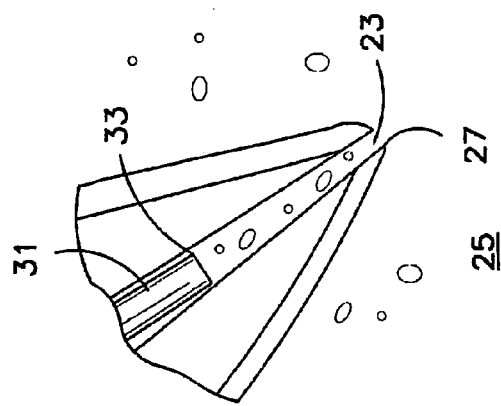
Figure 3A:
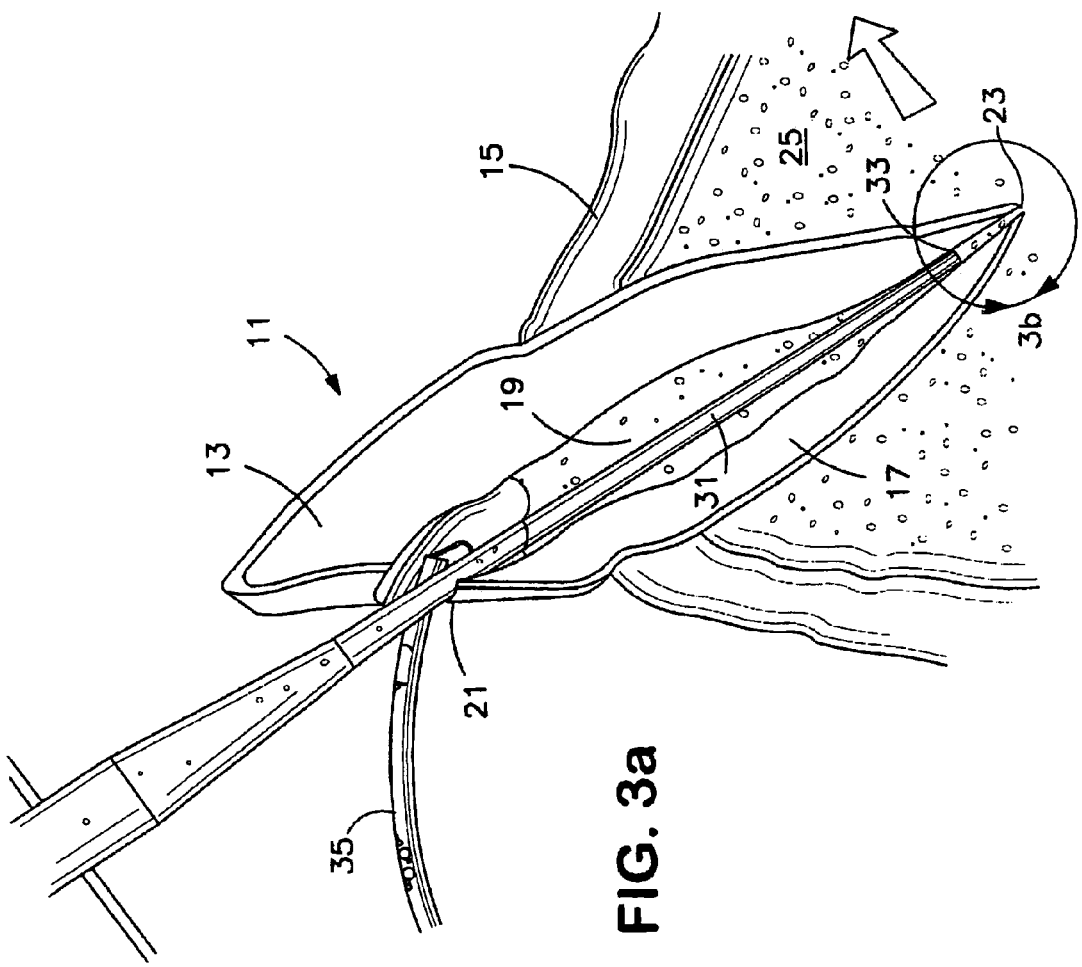
FIG. 3a is a cut away side view of a tooth showing a first aspirator and fluid delivery tube.

Referring now to FIG. 3a, the methods and apparatus used for the gross evacuation of the coronal portion of the root canal will now be explained. A microaspirator 31 is inserted into the canal to a point 33 approximately 4–5 mm from the apex as seen in FIG. 3b. A suitable microaspirator for this purpose is a soft plastic microaspirator such as part number UP0341 available from Ultradent Products, Incorporated located in South Jordan, Utah. Of course, any comparable device may be used for this purpose. A vacuum is applied to the microaspirator as is well known in the art which results in debris being sucked up into the microaspirator. Specifics of a suitable delivery tube 35 and vacuum system are well known to persons skilled in the art.

A fluid delivery tube 35 is placed at the top of the coronal opening of the root canal at end 21 as shown in FIG. 3a and the desired irrigant is supplied by fluid delivery tube 35. A suction exists at point 33 of the microaspirator by virtue of an opening in the end of the tube adjacent to point 33 and the applied vacuum which results in the irrigant and remaining debris being drawn to the hole in the end of microaspirator at point 33. This irrigation and suction results in a nearly complete cleaning of the upper portion of the canal, i.e., the portion extending from the of the microaspirator at point 33 through the entire length of the canal to end 19. This occurs because as the irrigant is delivered via the delivery tube, the irrigant fills the root canal space combines with the debris and together are sucked down the root canal by virtue of the vacuum created at the end of delivery tube at point 33 and then up through microaspirator 31 by virtue of the vacuum created. This step normally takes several minutes to complete depending on the size of the root canal space. For example upper canine teeth have larger root canal spaces than lower incisors and require a longer initial irrigation. At the end of this phase the irrigant will be clear and devoid of gas bubbles formed by the dissolving necrotic tissue as well as particulate matter remaining from instrumentation.

It should be noted that although some irrigant may go past end 33, the 4–5 mm distance from apex 23 is sufficient to prevent any irrigant from reaching periapical tissue 25.

The gross evacuation of the canal debris in the upper portion of the root canal is critical to the proper completion of phase two since a much smaller tube is used to evacuate the apical portion, i.e., the bottom 4–5 mm of the root canal. This is because the debris in the upper portion of the root canal, prior to the evacuation performed by phase one, includes particles of a size which would clog the smaller opening of the microaspirator which is inserted into the apical portion of the root canal.

Figure 4B:
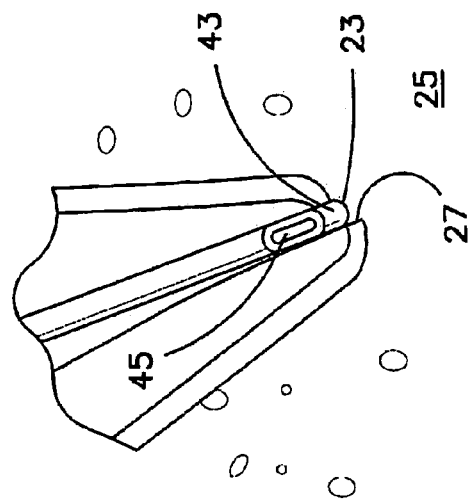
Figure 4A:
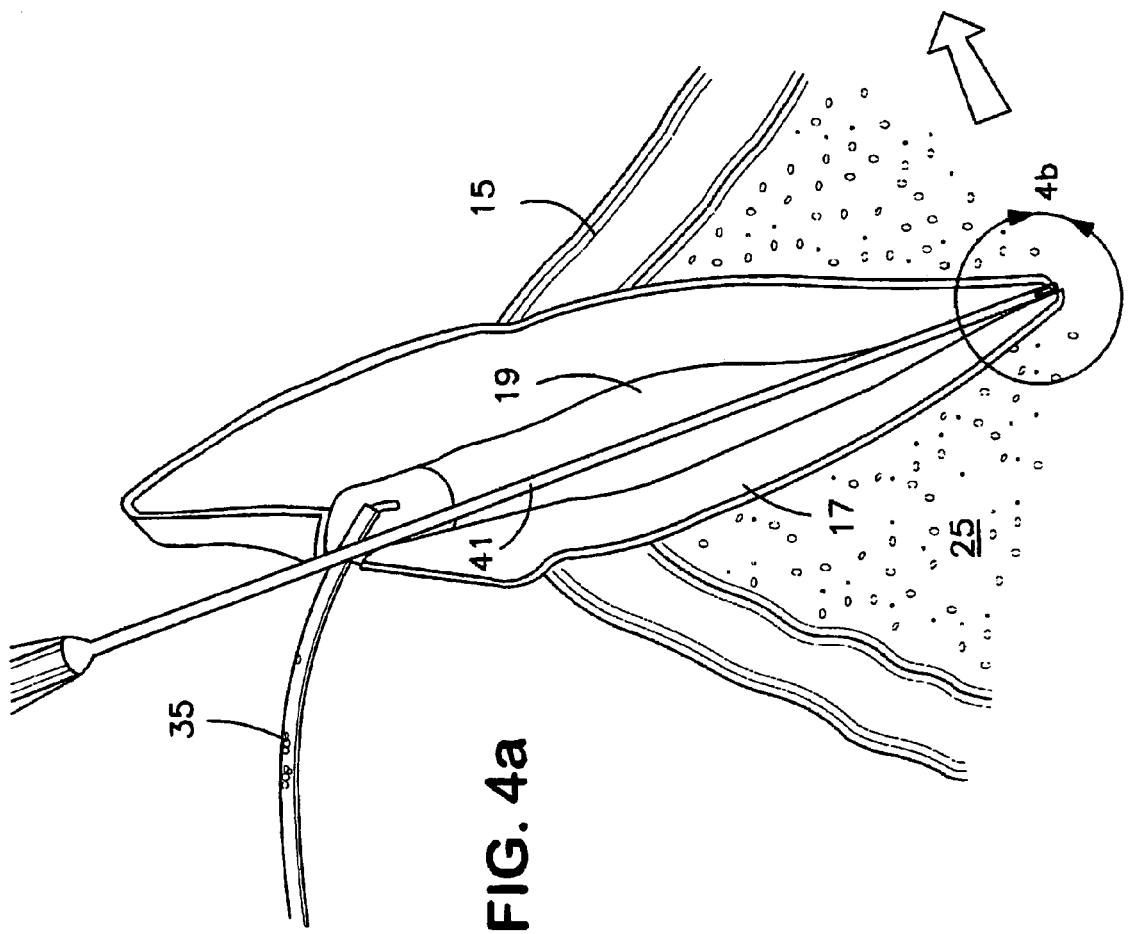
FIG. 4a is a cut away side view of a tooth showing a second aspirator and fluid delivery tube.

Phase two of the procedure will now be described with references to FIGS. 4a and 4b. In phase two, a microaspirator 41 is inserted into the root canal extending to the apex 23 as best seen in FIG. 4b. Microaspirator 41 is typically made of a metallic material such as stainless steel or titanium and in one embodiment, has an outside diameter of 0.014 inches. Its tip 43 is welded shut and rounded and includes a side vent approximately 0.75 mm long beginning at a point approximately 0.5 mm from the end of tip 43.

Of course, the foregoing dimensions and materials are provided by way of example of a specific embodiment. What is important is that microaspirator 41 be sized so as to be able to fit into the canal so that it extends substantially completely to apex 23 with side vent 45 extending as close to the end of the root as possible but without extending into the periapical tissue. Further, microaspirator 41 should be sized so that there is close contact between the root canal wall in the apical portion and the microaspirator. This is to ensure that some of the irrigant is drawn to the end of microaspirator 41 by capillary action.

As was the case in phase one, irrigant is delivered via delivery tube 35 and a vacuum is applied to microaspirator 41. In this manner, irrigant is drawn down into the root canal and into the apical portion of the root canal, that is, the bottom approximately 4–5 mm portion of the canal ending at apex 43. Since tip 43 is closed, irrigant is drawn into vent 45 and does not extend past tip 43 and cannot be drawn into apical tissue 25 due to the vacuum which exists at vent 45. By this technique, the irrigant flushes the apical portion of the root canal, removing out any remnants of debris which still exist in a manner which does not allow the irrigant to enter the periapical tissue.

Additionally, and importantly, in the event microaspirator 41 is accidentally forced into the periapical tissue, the side vent will become obstructed by the tissue and the vacuum which exists in the root canal ceases to exist. Since the irrigant in the canal is not under pressure, the irrigant will cease to be withdrawn by microaspirator 41 indicating to the practitioner that the microaspirator has extended too far and needs to be withdrawn back into the root canal space slightly, up to the point when the side vent is not in the periapical tissue at which point the irrigant again begins to be withdrawn.

I claim:

1. A method for irrigating a root canal of a tooth having a coronal end and an apex end, said canal having been shaped after removal of pulp material, said method comprising:
    a) inserting a first aspirator into the coronal end of the canal such that an end of said first aspirator is disposed partway within said canal, said end of said first aspirator having an opening;
    b) performing an evacuation of a coronal portion of the root canal by applying a vacuum to the first aspirator;
    c) placing a fluid delivery tube adjacent the coronal end of the canal;
    d) supplying fluid to said fluid delivery tube wherein the fluid is drawn to said opening of the first aspirator, said fluid being withdrawn from said canal by operation of said vacuum;
    e) removing said first aspirator and inserting a second aspirator into the canal, said second aspirator having a smaller diameter than said first aspirator and is sized so as to enable insertion of said second aspirator substantially completely to said apex end, said second aspirator being closed at said apex end and positioned such that a side vent of said second aspirator is adjacent said apex end;
    f) performing an evacuation of an apical portion of the root canal by applying a vacuum to said second aspirator wherein the fluid is drawn to said side vent of the second aspirator and is withdrawn from said canal by operation of said vacuum.

2. The method defined by claim 1 wherein said first aspirator is comprised of a plastic material.

3. The method defined by claim 1 wherein the end of said first aspirator is disposed approximately 5 mm from said apex end.

4. The method defined by claim 1 wherein said second aspirator is comprised of stainless steel.

5. The method defined by claim 1 wherein said coronal portion evacuation causes debris inside the canal to be withdrawn.

* * * * *